(12) United States Patent
Suzuki et al.

(10) Patent No.: US 10,085,710 B2
(45) Date of Patent: Oct. 2, 2018

(54) RADIOGRAPHING SYSTEM, METHOD OF CONTROLLING RADIOGRAPHING SYSTEM, AND RECORDING MEDIUM OF COMPUTER PROGRAM

(71) Applicant: CANON KABUSHIKI KAISHA, Tokyo (JP)

(72) Inventors: Masataka Suzuki, Kawasaki (JP); Shichihei Sakuragi, Tokyo (JP); Ryo Suzaki, Tokyo (JP); Motoki Tagawa, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 247 days.

(21) Appl. No.: 15/094,588

(22) Filed: Apr. 8, 2016

(65) Prior Publication Data

US 2016/0302753 A1 Oct. 20, 2016

(30) Foreign Application Priority Data

Apr. 15, 2015 (JP) ................................. 2015-083722

(51) Int. Cl.
*H05G 1/64* (2006.01)
*A61B 6/00* (2006.01)

(52) U.S. Cl.
CPC .............. *A61B 6/56* (2013.01); *A61B 6/4266* (2013.01); *A61B 6/5241* (2013.01); *A61B 6/547* (2013.01); *A61B 6/4233* (2013.01); *A61B 6/461* (2013.01); *A61B 6/54* (2013.01)

(58) Field of Classification Search
CPC ... A61B 6/5235; A61B 6/4266; A61B 6/4233; A61B 6/56; A61B 6/461; A61B 6/54; A61B 6/5241; A61B 6/547
See application file for complete search history.

(56) References Cited

U.S. PATENT DOCUMENTS

2016/0135764 A1* 5/2016 Wojcik ................. A61B 6/4233
378/62

FOREIGN PATENT DOCUMENTS

JP 2012-040141 A 3/2012

\* cited by examiner

*Primary Examiner* — Courtney Thomas
(74) *Attorney, Agent, or Firm* — Canon USA Inc., IP Division

(57) ABSTRACT

A radiographing system includes a plurality of radiation imaging apparatuses and a composition processing unit which composites a plurality of radiation images acquired from the plurality of radiation imaging apparatuses to generate a long-length image. Each of the radiation imaging apparatuses includes a radiation detecting panel which has a plurality of pixels arrayed in a two-dimensional matrix and converts radiated radiation into an image signal, and a position acquiring unit which acquires positional information by communicating with an external apparatus. A position deciding unit decides an order, in which the plurality of radiation images to be composited by the composition processing unit are composited, based on the positional information acquired by the position acquiring unit.

16 Claims, 5 Drawing Sheets

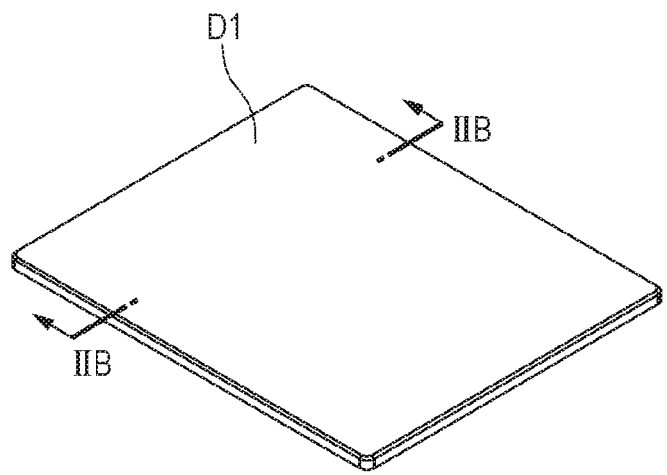
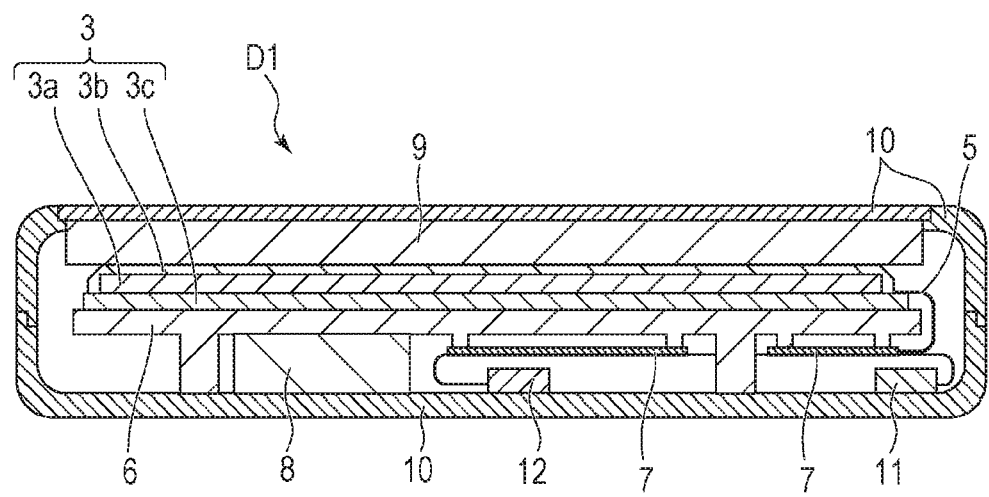

RADIOGRAPHING SYSTEM, METHOD OF CONTROLLING RADIOGRAPHING SYSTEM, AND RECORDING MEDIUM OF COMPUTER PROGRAM

BACKGROUND OF THE INVENTION

Field of the Invention

The present invention relates to a radiographing system using a plurality of radiation imaging apparatuses, a method of controlling the radiographing system to generate a long-length radiographic image, and a recording medium storing therein a computer program.

Description of the Related Art

In recent years, for example, in the medical field, there has been a demand for photography having a long-length observation region (hereinafter, referred to as long-length photography) such as photography of an entire of the spinal cord or the lower limbs or the whole body for grasping a distortion or an abnormality of an examinee.

Japanese Patent Laid-Open No. 2012-040141 discloses a radiographing system which obtains a long-length image (image obtained by long-length photography) by arranging a plurality of radiation imaging apparatuses to perform photography and compositing radiation images photographed by the respective radiation imaging apparatuses. In the radiographing system of Japanese Patent Laid-Open No. 2012-040141, indexes having predetermined shapes and sizes are arranged so as to be captured in the respective radiation images photographed by the plurality of radiation imaging apparatuses at a time of the long-length photography. The radiographing system then discriminates the indexes captured in the respective radiation images and judges an order in which the respective radiation images are to be connected.

In the radiographing system described in Japanese Patent Laid-Open. No. 2012-040141, since the indexes captured in the radiation images are discriminated, the discrimination becomes difficult in a case where the indexes are difficult to be arranged at appropriate positions in an irradiation field. On the other hand, when positions of the indexes are fixed so as to be arranged in the irradiation field, the indexes overlap with a structure of an object or body part in the radiation images, so that recognition of the indexes becomes difficult.

Accordingly, the invention provides a radiographing system which generates a long-length image by compositing a plurality of radiation images and which is capable of easily deciding an order in which the radiation images are connected.

SUMMARY OF THE INVENTION

One aspect of the invention is a radiographing system, including: a plurality of radiation imaging apparatuses each of which has a radiation detecting panel, which has a plurality of pixels arrayed in a two-dimensional matrix and converts radiated radiation into an image signal; and a composition processing unit which composites a plurality of radiation images acquired from the plurality of radiation imaging apparatuses to generate a long-length image, in which each of the plurality of radiation imaging apparatuses includes a position acquiring unit which acquires positional information, and a position deciding unit which decides an order, in which the plurality of radiation images to be composited by the composition processing unit are composited, based on the positional information acquired by the position acquiring unit is provided.

Further features of the present invention will become apparent from the following description of exemplary embodiments with reference to the attached drawings.

BRIEF DESCRIPTION OF THE DRAWINGS

FIGS. 2A and 2B are views illustrating radiation imaging apparatuses in the first exemplary embodiment.

DESCRIPTION OF THE EMBODIMENTS

Exemplary embodiments of the invention will be specifically described below with reference to attached drawings. However, details of sizes or structures indicated in the respective exemplary embodiments are not limited by the specification or the drawings. Note that, in this specification, radiation includes X-rays, and can also include α rays, β rays, γ rays, particle rays, cosmic rays, and the like.

First Exemplary Embodiment

Figure 1:
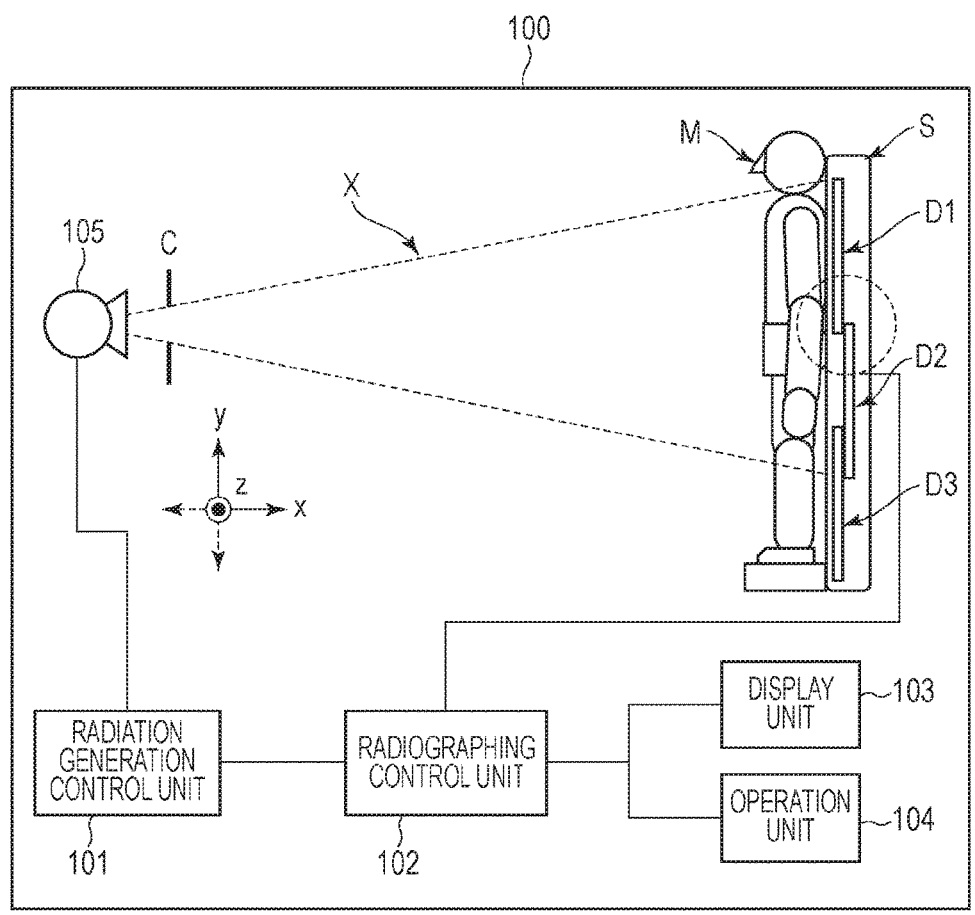
FIG. 1 is a view illustrating a radiographing system in a first exemplary embodiment.

First, a radiographing system 100 will be described by using FIG. 1. The radiographing system 100 performs examination (photography) based on an examination order including a plurality of pieces of examination information. The examination information includes information of photographing protocols, and the photographing protocols respectively specify a photographing condition, a content of image processing applied to a photographed image, or the like. More specifically, the photographing protocols include parameter information or photographing implementation information, which is used at a time of the photography, at a time of the image processing, or the like, and photographing environment information such as, for example, a type of a sensor or a photographic posture. Moreover, the examination information includes information, which specifies the examination order or which specifies a photographed image according to the examination order, such as an examination ID and a receipt number, in the case of implementing long-length photography, the radiographing system 100 connects and composites radiation images acquired by respective radiation imaging apparatuses so that a photographing range is spread. In this case, by recognizing a relative positional relationship of the respective radiation imaging apparatuses, the radiographing system 100 is able to determine in what order the respective radiation images are to be connected. Then, it becomes possible for the radiographing system 100 to execute, based on the determination, composition processing of compositing the radiation images photographed by the respective radiation imaging apparatuses and to display a long-length image on a display unit or the like.

The radiographing system 100 includes at least a radiographing control unit 102 (e.g., a computer including a programmable microprocessor) and a plurality of radiation imaging apparatuses (D1, D2, and D3). An example of a radiation imaging apparatus is a radiographic sensor, such as an X-ray flat panel detector (FPD). Each of the plurality of radiation imaging apparatuses D1, D2, and D3 includes a position acquiring unit which acquires positional information (11 in FIG. 2B and FIG. 3). The radiographing control unit 102 has a position deciding unit which decides an order, in which a plurality of radiation images are composited, based on the positional information acquired by the position acquiring unit 11 (1021 in FIG. 3). The radiographing system 100 further includes a radiation generation control unit 101, a display unit 103, an operation unit 104, and a radiographic table or stand S. Though the radiographing system 100 in the present exemplary embodiment is composed of three radiation imaging apparatuses D1, D2, and D3, there is no limitation thereto, and the radiographing system 100 may be composed of two radiation imaging apparatuses or four or more radiation imaging apparatuses. The radiographing system 100 generates an image that a composition processing unit (1022 in FIG. 3) composites images (radiation images) respectively acquired by the radiation imaging apparatuses D1, D2, and D3, and is thereby able to obtain a long-length image. An example of the long-length image includes an image obtained by compositing radiation images in a case where the plurality of radiation imaging apparatuses D1, D2, and D3 are irradiated with radiation simultaneously. Further, the long-length image may be an image obtained by compositing radiation images acquired by sequentially irradiating the plurality of radiation imaging apparatus D1, D2, and D3 with radiation with a predetermined time difference. The radiation images here are images obtained by detecting radiation by the radiation imaging apparatuses D1, D2, and D3, and acquiring image data. Each unit of the radiographing system 100 will be described below.

A radiation source 105 has a function of irradiating the plurality of radiation imaging apparatus D1, D2, and D3 with radiation. Here, the radiation source 105 is an X-ray tube in the present exemplary embodiment, and irradiates an object M (that is, an examinee) with radiation (here, X-rays). A collimator C which restricts an irradiation region of radiation is arranged between the radiation source 105 and the examinee M.

The radiation generation control unit 101 (e.g., a computer including a programmable microprocessor) controls generation of radiation based on control of the radiographing control unit 102. Specifically, the radiation generation control unit 101 generates radiation by applying a voltage to the radiation source 105 in accordance with a photographing condition corresponding to a photographing protocol. In addition, the radiation generation control unit 101 is able to control the collimator C for adjusting an irradiation field and an intensity of radiation.

Each of the plurality of radiation imaging apparatuses D1, D2, and D3 acquires a radiation image based on radiation which has been transmitted through the examinee M. Moreover, each of the plurality of radiation imaging apparatuses D1, D2, and D3 may be configured integrally with the radiographic table S or may be configured separately where the radiation imaging apparatuses D1-D3 are removably attached to the radiographic table or stand S.

Here, a part of the plurality of radiation imaging apparatuses D1, D2, and D3 spatially overlaps with one or more of the other radiation imaging apparatuses. In the present exemplary embodiment, the plurality of radiation imaging apparatuses D1, D2, and D3 are arranged so that the radiation imaging apparatuses D1 and D3 partially overlap with an effective pixel region of the radiation imaging apparatus D2 with a space. Therefore, among image signals obtained in the radiation imaging apparatus D2, a signal obtained from a pixel spatially overlaps with the radiation imaging apparatus D1 and/or D3 is caused to be lowered. That is, in a region which is in a long-length image after compositing radiation images and in which the radiation images of the plurality of radiation imaging apparatuses overlap, an artifact (false image or defect part) can be generated. Here, "spatially overlapping" may mean that the radiation imaging apparatuses overlap with each other with direct or indirect physical connection or overlap without physical connection and with a space therebetween.

The radiographic table S regulates arrangement of the plurality of radiation imaging apparatuses D1, D2, and D3. That is, the radiographic table S has a function as a holding unit which holds the plurality of radiation imaging apparatuses D1, D2, and D3. Here, the radiographic table S (holding unit) is arranged in an upper side of a position at which the radiation imaging apparatus D1 faces the radiation source 105. Further, the radiographic table S is arranged in a lower side of a position at which the radiation imaging apparatus D3 faces the radiation source 105. In addition, the radiation imaging apparatus D2 is arranged on a side of rear surfaces of the radiation imaging apparatuses D1 and D3 in a lower side of the radiation imaging apparatus D1 and in an upper side of the radiation imaging apparatus D3. When the examinee M stands on a step tool placed in front of the radiographic table S, a position of the examinee M with respect to the radiographic table S and the radiation source 105 is regulated.

The radiographing control unit 102 integrally controls processing of radiographing based on a photographing condition. The radiographing control unit 102 has functions as a transmission unit and a reception unit for transmitting and receiving various information to and from the radiation generation control unit 101. Moreover, the radiographing control unit 102 performs image processing for photographed images obtained from the respective radiation imaging apparatuses D1, D2, and D3. The image processing includes composition processing, correction processing, gradation processing, frequency processing, and the like of the plurality of photographed images from the respective radiation imaging apparatuses D1, D2, and D3. The composition processing is performed by the composition processing unit 1022 which will be described below. The radiographing control unit 102 displays the obtained photographed images and a long-length image obtained by compositing them on the display unit 103. In addition, the radiographing control unit 102 is also able to transmit the obtained long-length image to a PACS or a printer.

The display unit 103 displays information of state of the radiographing system 100 or the like and the long-length image to an operator. That is, the display unit 103 functions as a display unit which displays states of the plurality of radiation imaging apparatuses D1, D2, and D3 and the long-length image. In addition, the display unit 103 may display a state of only a part of the plurality of radiation imaging apparatuses D1, D2, and D3. The display unit 103 can be a display, for example. The display unit 103 may also display, for example, an examination order received from an RIC or an examination order created by the operator of the radiographing system 100.

The operation unit 104 acquires an instruction from the operator. The operation unit 104 includes at least any one of a graphical user interface (GUI) or various input units such as, for example, a keyboard, a mouse, and a touch panel. For example, via the operation. unit 104, the operator is able to input, to the radiographing control unit 102, an instruction of image copying, a selection of the radiation imaging apparatus to use for photography, a change in a protocol, or the like.

Description will be given for one radiation imaging apparatus D1 among the plurality of radiation imaging apparatuses D1, D2, and D3 by using FIGS. 2A and 2B. FIG. 2A is a view illustrating an external appearance of the radiation imaging apparatus D1. FIG. 2B illustrates a sectional view taken along an IIB-IIB direction in FIG. 2A. Though a function of the radiation imaging apparatus D1 will be described in the description below, each of the other radiation imaging apparatuses D2 and D3 also has a similar function.

The radiation imaging apparatus D1 has at least a radiation detecting panel 3 and a position acquiring unit 11.

As the radiation detecting panel 3, a radiation detecting panel of a direct conversion type which converts radiation such as a-Se directly into an electric signal, or a radiation detecting panel of an indirect type which uses a phosphor layer such as a Cesium-Iodide (CsI) scintillator layer, and a photoelectric conversion element can be used. Though the radiation detecting panel of the indirect type will be described in the present exemplary embodiment, there is no limitation thereto, as a direct-type radiation detecting panel is equally applicable.

The radiation detecting panel 3 has a plurality of pixels arrayed in a two-dimensional matrix. Each of the plurality of pixels has a photoelectric conversion element and a TFT. The radiation detecting panel 3 has a sensor substrate 3c on which the plurality of pixels are arranged, a phosphor layer 3a which is arranged on the sensor substrate 3c, and a protection film 3b. The protection film 3b is made of a material having low moisture permeability, and has a function for protecting the phosphor layer 3a.

The radiation detecting panel 3 is electrically connected to a control substrate 7 via a flexible circuit substrate 5. The control substrate 7 reads out a signal based on radiation detected from the radiation detecting panel 3. The control substrate 7 can perform processing for the signal and convert it into a radiation image.

The position acquiring unit 11 acquires positional information by communicating with an external apparatus. The position acquiring unit 11 includes a wireless communication antenna for performing wireless communication with the external apparatus. Here, the external apparatus refers to an apparatus which can hold and provide positional information. Moreover, the positional information refers to a distance from the radiation imaging apparatus D1 to a predetermined reference position. Examples of the predetermined reference position include a position of the radiation source 105, a position of a floor, and one or more positions of the other radiation imaging apparatuses D2 and D3. That is, the positional information includes information regarding at least any one of a distance from the radiation source 105 to the radiation imaging apparatus D1, a distance from the floor, and a relative distance from or positional relationship with one or more of the other radiation imaging apparatuses D2 and D3. For example, by using height information (positional information in a gravity direction) estimated by the radiation imaging apparatus D1, a relative height relationship with each of the radiation imaging apparatuses D2 and D3 can be specified.

The position acquiring unit 11 acquires the positional information by, for example, a wireless access point in a facility or a hospital, in which the radiographing system 100 is used, and the wireless communication antenna. That is, the external apparatus in the present exemplary embodiment refers to, for example, the wireless access point or a system in a hospital, which is connected to the wireless access point. The position acquiring unit 11 estimates a position based on information from the wireless access point. That is, the position acquiring unit 11 can perform estimation of the position by acquiring a radio wave intensity of a radio wave transmitted from the wireless access point, a difference in times at which the radio wave reaches, or an arriving angle of the radio wave, in a case where the wireless antenna receives the radio wave. Here, in a case where the estimation of the position is not stable due to influence of an environment or the like, it may be considered that the positional information is estimated erroneously. Thus, in a case where an erroneous positional relationship is estimated, the position acquiring unit 11 is able to perform notification. Moreover, in the radiation imaging apparatus D1, an LED, which is capable of emitting light of a plurality of colors for performing display to the outside based on the notification, or the like may arranged, and a color to be developed may be changed according to a relative position. The radiation imaging apparatus D1 may also cause the display unit 103 to perform display, via the radiographing control unit 102. Thereby, the operator is able to determine whether the estimated positional information is erroneous.

The position acquiring unit 11 is able to acquire the positional information by a method other than the method using the wireless access point. The position acquiring unit 11 may have an altimeter or a barometer by which a height from the radiation imaging apparatus D1, in which the position acquiring unit 11 itself is incorporated, to a floor surface or from a specific reference position. Moreover, the position acquiring unit 11 may have a GPS (Global Positioning System) and estimate a distance from a predetermined reference position. Alternatively, the position acquiring unit 11 may have a measuring unit such as a laser displacement gauge and estimate the height from the radiation imaging apparatus D1, in which the position acquiring unit 11 itself is incorporated, to the floor surface.

Other configurations in the radiation imaging apparatus D1 illustrated in FIG. 2B will be described. As illustrated in FIG. 2S, the radiation imaging apparatus D1 may include a rechargeable battery 8 for supplying electric power to the radiation detecting panel 3, the control substrate 7, and the like. Further, the method of supplying electric power is not limited thereto, and electric power may be supplied from outside by connection in a wired or wireless manner.

The radiation imaging apparatus D1 further has a housing 10 which accommodates the radiation detecting panel 3. In the housing 10, a buffer material 9 which protects the radiation detecting panel 3 from an impact or the like from outside may be stored. The radiation detecting panel 3 is supported by a supporting unit base 6 so as to be regulated to be in a predetermined arrangement. In addition, the radiation imaging apparatus D1 has a communication unit 12 which transmits/receives various information to/from the radiographing control unit 102 and transmits a radiation image. The communication unit 12 is electrically connected to the control substrate 7 and the position acquiring unit 11 in a wired or wireless manner, and transmits/receives the various information and the radiation image to/from them. Further, the position acquiring unit 11 may have a function of the communication unit 12, or the control substrate 7 may have functions of the position acquiring unit 11 and the communication unit 12.

Figure 3:
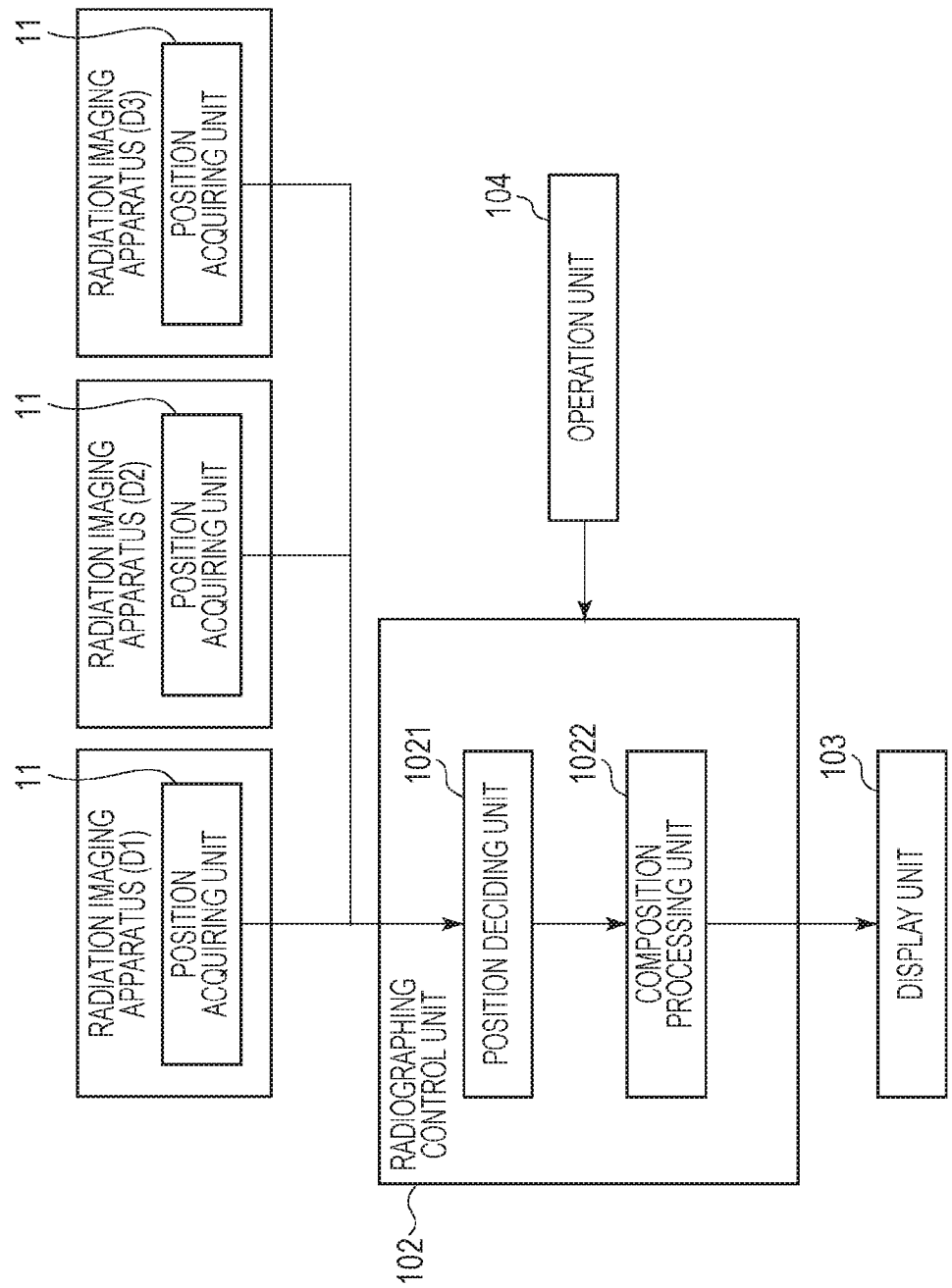
FIG. 3 is a view illustrating a radiographing control unit in the first exemplary embodiment.

Processing performed in the radiation imaging apparatuses D1, D2, and D3 and the radiographing control unit 102 will be described by using FIG. 3.

First, the position acquiring unit 11 arranged in each of the plurality of the radiation imaging apparatuses D1, D2, and D3 acquires positional information of the radiation imaging apparatus D1, D2, or D3, in which the position acquiring unit 11 itself is arranged, by any of the methods described above. Next, the communication unit 12 transmits the positional information acquired by the position acquiring unit 11 to the radiographing control unit 102 (position deciding unit 1021).

The position deciding unit 1021 then decides an order, in which a plurality of radiation images to be composited by the composition processing unit 1022 are composited, based on the positional information acquired by the position acquiring unit 11. In the present exemplary embodiment, based on positional information regarding the height from the floor surface, the position deciding unit 1021 decides the order as the radiation imaging apparatus D1, the radiation imaging apparatus D2, and the radiation imaging apparatus D3 in a descending order of the height (distance in the gravity direction). Further, based on positional information regarding the distance from the radiation source 105, the position deciding unit 1021 judges that the radiation imaging apparatuses D1 and D3 are positioned nearer than the radiation imaging apparatus D2. Accordingly, it is possible to judge that, when obtaining a long-length image by composition, the radiation images are to be connected in an order of the radiation image acquired by the radiation imaging apparatus D1, the radiation image acquired by the radiation imaging apparatus D2, and the radiation image acquired by the radiation imaging apparatus D3 from the top. As to a region in which a plurality of radiation images overlap with each other, the position deciding unit 1021 can make a judgment (determination), such that the radiation image acquired by the radiation imaging apparatus which is arranged nearer is used preferentially, in order to reduce influence of a reflection image.

Before acquiring the radiation images from the plurality of radiation imaging apparatuses D1, D2, and D3, it is possible to perform acquisition of the positional information by the position acquiring unit 11 and decision of the order, in which the plurality of radiation images are composited, by the position deciding unit 1021. That is, before long-length photography is performed, it is possible to know success or failure of arrangement and an arrangement order of the respective radiation imaging apparatuses D1, D2, and D3.

The composition processing unit 1022 composites the plurality of radiation images, which are acquired from the plurality of radiation imaging apparatuses D1, D2, and D3, based on the order decided by the position deciding unit 1021, and generates a long-length image. The plurality of radiation images are radiation image data acquired by each of the plurality of radiation imaging apparatuses D1, D2, and D3. The radiation image acquired from the radiation imaging apparatus D2 among the radiation images has artifact generated in a region in which the radiation imaging apparatuses overlap. The composition processing unit 1021 is able to minimize an area of the artifact, which is generated in the long-length image, by generating the long-length image by using the radiation image acquired from the radiation imaging apparatus D1, as to a region in which the radiation imaging apparatuses D1 and D2 overlap (defect region).

After this processing, the radiographing control unit 102 can display the corrected long-length image on the display unit 103. Furthermore, whether the position acquiring unit 11 succeeded in recognizing the position correctly may be displayed on the display unit 103. By each processing which has been described by using FIG. 3, the radiographing system 100 is able to acquire the order of the radiation imaging apparatuses D1, D2, and D3 before the long-length photography. Therefore, the radiographing system 100 is also able to confirm whether or not the respective radiation imaging apparatuses D1, D2, and D3 are succeeded in being arranged correctly, in advance.

As above, in the radiographing system 100 in the present exemplary embodiment, the positional information is able to be specified without connecting a separate body to the radiation imaging apparatuses D1, D2, or D3 in a wired manner. Moreover, each of the radiation imaging apparatuses D1, D2, and D3 can specify (estimate) the own position by the position acquiring unit 11. Accordingly, when connecting and compositing the plurality of radiation images, it is possible to judge in what order the composition is to be performed. Further, it is possible to know the success or failure of the arrangement and the arrangement order of the respective radiation imaging apparatuses D1, D2, and D3, before the long-length photography is performed. Thus, it is possible to suppress work mistakes in preparation of the photography and perform composition processing of the radiation images appropriately. Furthermore, since it is possible to decide (a priori) the order, in which the plurality of radiation images are connected and composited, without using the radiation images, the indexes can be easily recognized.

Second Exemplary Embodiment

Figure 4:
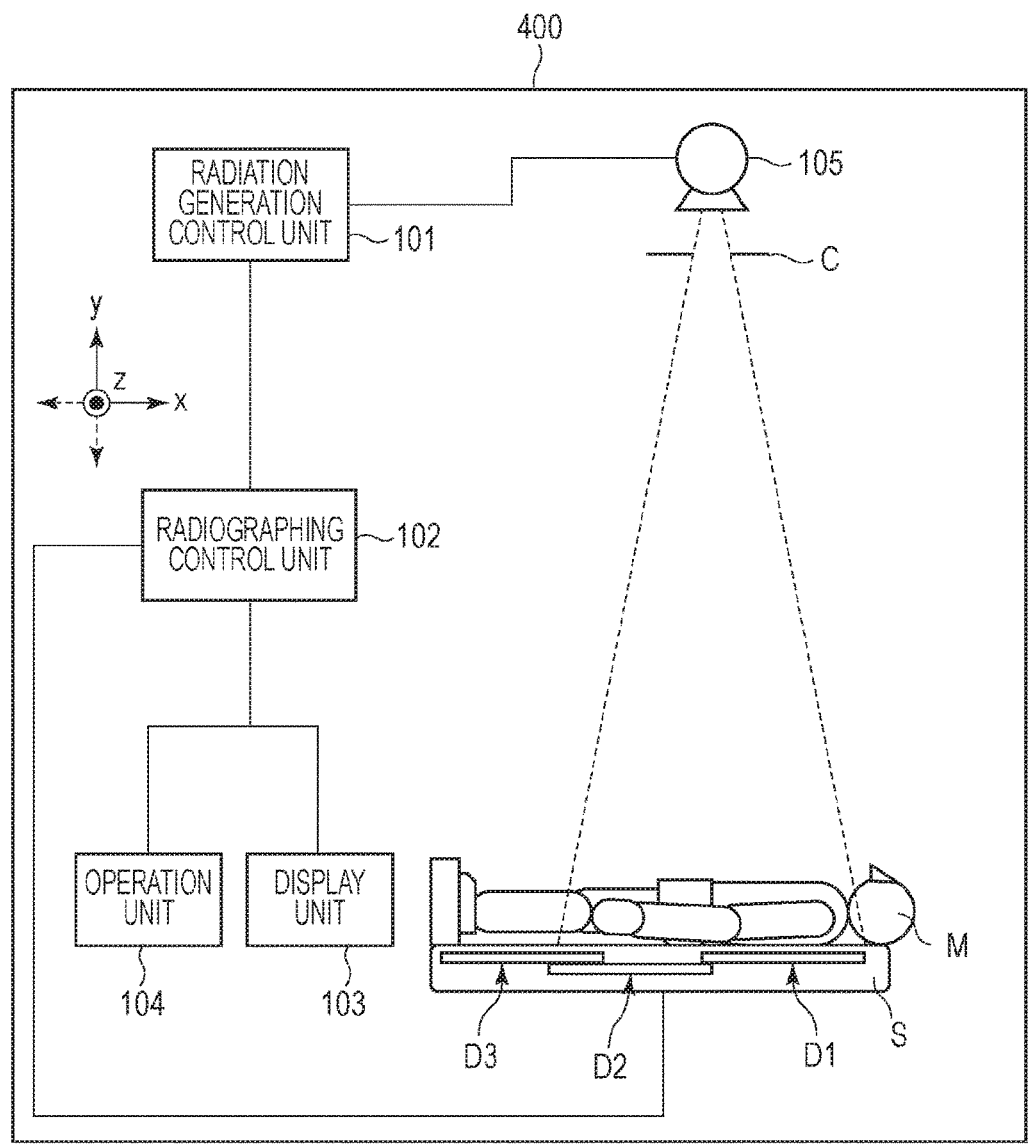
FIG. 4 is a view illustrating a radiographing system in a second exemplary embodiment.
Figure 5:
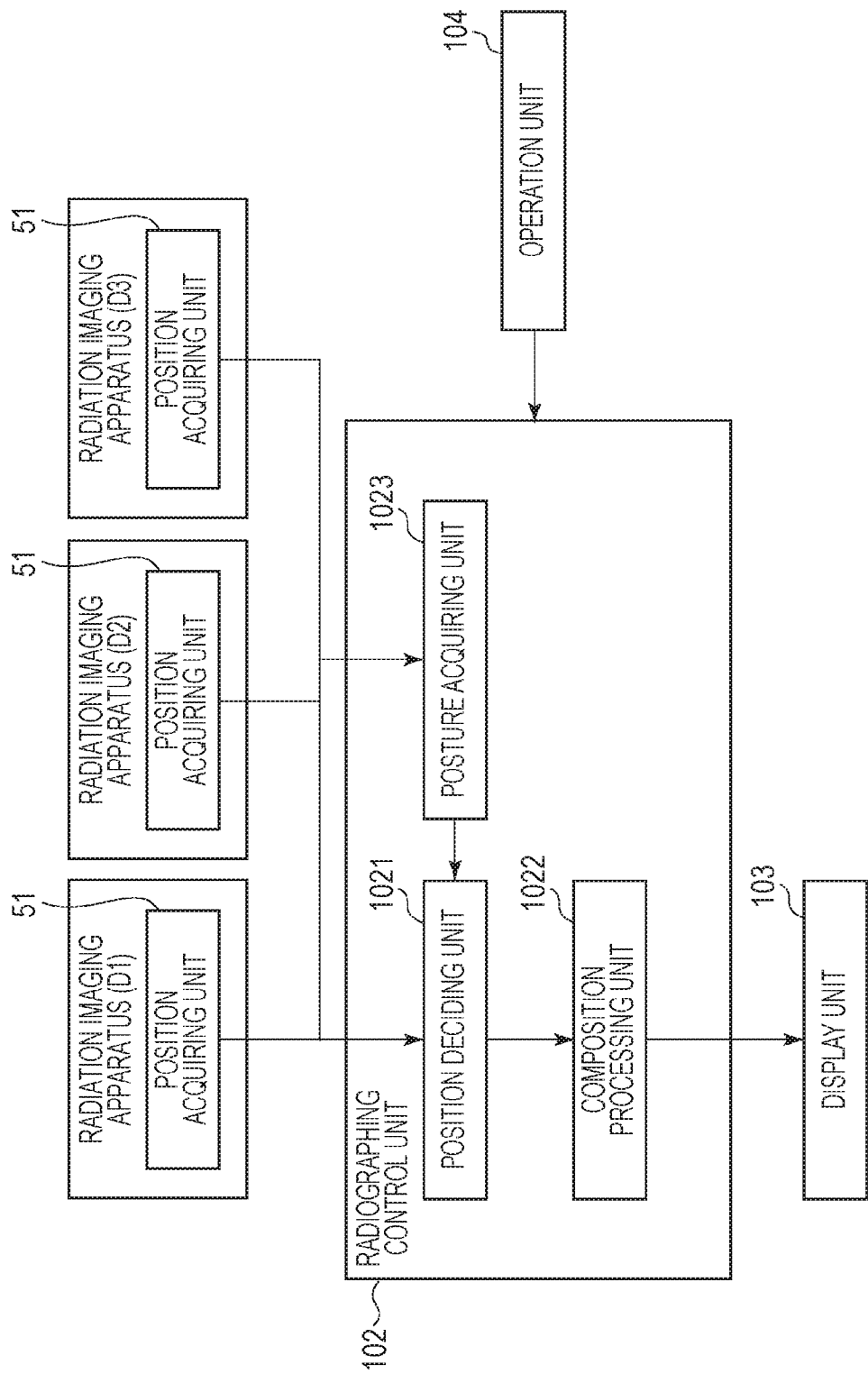
FIG. 5 is a view illustrating a radiographing control unit in the second exemplary embodiment.

Next, a second exemplary embodiment will be described by using FIG. 4 and FIG. 5. First, a difference between the present exemplary embodiment and the first exemplary embodiment will be described. In the first exemplary embodiment, a case where the radiographing system 100 performs long-length photography in a state where an examinee is in an upright position has been described. A radiographing system in the second exemplary embodiment can perform long-length photography not only in the upright position but also in a supine position (or a prone position) as illustrated in FIG. 4. The radiographing system thus performs processing of deciding the order, in which the plurality of radiation images are composited, based on information regarding postures of the radiographic table S and the radiation imaging apparatuses D1, D2, and D3.

As illustrated in FIG. 4, an upright position state is a state where the plurality of radiation imaging apparatuses D1, D2, and D3 are arranged so that an area to be photographed is spread in the height direction (gravity direction) in accordance with the postures of the radiographic table S and the radiation imaging apparatuses D1, D2, and D3. A supine position state is a state where the plurality of radiation imaging apparatuses D1, D2, and D3 are arranged so that the area to be photographed is spread in an approximately horizontal direction (direction perpendicular to the gravity direction).

In a case where the radiographic table S is transformed, a radiographing system 400 changes information for estimating the relative positional relationship of the radiation imaging apparatuses D1, D2, and D3 in order to cope with various photographing states such as the upright position and the supine position. For example, at a time of the upright position, the radiographing system 400 is able to decide, by using positional information in the height direction, the order when connecting the radiation images, but, at a time of the supine position, it is difficult to decide the order when the connection is performed, from the positional information of the height direction.

Processing performed in the radiation imaging apparatuses D1, D2, and D3 and the radiographing control unit 102 will be described by using FIG. 5. A position acquiring unit 51 in the present exemplary embodiment has a function as a posture estimating unit in addition to the function of the position acquiring unit 11 in the first exemplary embodiment. The posture estimating unit has a function of estimating a posture of the radiation imaging apparatus. The posture estimating unit has an acceleration sensor, and is able to calculate an angle of the gravity direction and the radiation imaging apparatus. From this angle, the radiation imaging apparatus is able to acquire information regarding the postures such as the upright position or the supine position. The information regarding the postures is information indicating the postures of the radiographic table S and the radiation imaging apparatus. The radiation imaging apparatus then transmits the information regarding the postures and the positional information to the radiographing control unit 102 by the communication unit 12. The communication unit 12 may cause the display unit 103 to display the information regarding the postures, via the radiographing control unit 102.

A posture acquiring unit 1023 acquires information regarding the postures of the plurality of radiation imaging apparatuses D1, D2 and D3 based on the information estimated by each posture estimating unit. The posture acquiring unit 1023 is able to select information suitable for determining the relative positional relationship of the respective radiation imaging apparatuses D1, D2, and D3 from the positional information acquired by the position acquiring units 51, based on the information regarding the postures. For example, in the case of photography in the supine position, it is suitable to judge the positional relationship by using the positional information of the horizontal direction as the positional information for grasping the positional relationship. Thus, the relative positional relationship of the radiation imaging apparatuses D1, D2, and D3 is judged by using the positional information of the horizontal direction.

The posture acquiring unit 1023 can acquire the postures by the information regarding the postures from at least one radiation imaging apparatus among the plurality of radiation imaging apparatuses D1, D2, and D3. This is because the plurality of radiation imaging apparatuses D1, D2, and D3 can take the same postures at the time of long-length photography. In addition, the posture acquiring unit 1023 may make a judgment (or determination) based on the positional information from two or more radiation imaging apparatuses.

The position deciding unit 1021 decides an order, in which the plurality of radiation images are composited, based on the information acquired by the posture acquiring unit 1023 and the positional information. The subsequent processing is similar to that of the first exemplary embodiment.

Though each of the radiation imaging apparatuses D1, D2, and D3 has the function of estimating the postures in the present exemplary embodiment, there is no limitation thereto. For example, the radiographic table S (hereinafter, holding unit S) may have the function of estimating the postures of the radiation imaging apparatuses D1, D2, and D3. Alternatively, the radiographing control unit 102 may acquire a value of the sensor directly from the acceleration sensor in each of the radiation imaging apparatuses D1, D2, and D3, and acquire the information regarding the postures by the posture acquiring unit 1023. Moreover, the position deciding unit 1021 may recognize the postures from positional information regarding a direction, which has a greater difference, among positional information of the respective plurality of radiation imaging apparatuses D1, D2, and D3. For example, in the case of photography in the upright position, positional information regarding the height direction has the greater difference. Moreover, in the case of photography in the supine position, positional information of a direction perpendicular to the gravity direction has the greater difference. Thus, the position deciding unit 1021 is able to discriminate the postures of the radiation imaging apparatuses D1, D2, and D3 and the relative positional information from the positional information. In addition, the radiographing system 400 has a plurality of functions of estimating the postures which are described above, and is also able to improve reliability by combining the function.

As above, the radiographing system 400 in the present exemplary embodiment is able to easily determine the order in which radiation images are to be connected, even when there is a change in a photographing state in long-length photography, such as the upright position and the supine position.

Further, the radiation imaging apparatuses D1, D2, and D3 described in the respective exemplary embodiments is usable even in a radiographing system which does not perform long-length photography. For example, an operator is able to acquire a radiation image by one radiation imaging apparatus and adopt this as one diagnostic image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application. No. 2015-083722, filed on Apr. 15, 2015, which is hereby incorporated by reference herein in its entirety.

What is claimed is:

1. A radiographing system, comprising:
a plurality of radiation imaging apparatuses each of which has a radiation detecting panel, the radiation detection panel having a plurality of pixels arrayed in a two-dimensional matrix and converts radiated radiation into an image signal;
a composition processing unit which composites a plurality of radiation images acquired from the plurality of radiation imaging apparatuses to generate a long-length image, wherein
each of the plurality of radiation imaging apparatuses includes a position acquiring unit which acquires positional information by communicating with an external apparatus; and
a position deciding unit which decides an order, in which the plurality of radiation images to be composited by the composition processing unit are composited, based on the positional information acquired by the position acquiring unit.

2. The radiographing system according to claim 1, wherein the position acquiring unit communicates with the external apparatus by using a wireless communication antenna.

3. The radiographing system according to claim 1, wherein the position acquiring unit acquires a distance from the radiation imaging apparatus to a predetermined reference position as the positional information.

4. The radiographing system according to claim 3, wherein the position acquiring unit acquires the positional information by using a GPS, an altimeter, or a laser displacement gauge.

5. The radiographing system according to claim 1, wherein the positional information acquired by the position acquiring unit for each of the plurality of radiation imaging apparatuses includes information regarding at least any one of a distance from a radiation source to, a distance from a floor to, and a relative distance from or positional relationship with, one or more of the other radiation. imaging apparatuses.

6. The radiographing system according to claim 1, further comprising:
a posture acquiring unit which acquires information regarding a posture of at least one radiation imaging apparatus among the plurality of radiation imaging apparatuses, wherein
the position deciding unit decides the order, in which the plurality of radiation images are composited, based on the information acquired by the posture acquiring unit and the positional information.

7. The radiographing system according to claim 1, further comprising
a holding unit which holds the plurality of radiation imaging apparatuses, and
a posture acquiring unit which acquires information regarding a posture of the holding unit, wherein
the position deciding unit decides the order, in which the plurality of radiation images are composited, based on the information acquired by the posture acquiring unit and the positional information.

8. The radiographing system according to claim 7, wherein
at least one radiation imaging apparatus among the plurality of radiation imaging apparatuses includes a posture estimating unit which estimates a posture of the one radiation imaging apparatus, and
the posture acquiring unit acquires information regarding postures of the plurality of radiation imaging apparatuses based on information estimated by the posture estimating unit.

9. The radiographing system according to claim 1, wherein the position acquiring unit acquires the positional information before acquiring the radiation images from the plurality of radiation imaging apparatuses.

10. The radiographing system according to claim 1, wherein the position deciding unit decides the order in which the composition processing unit composites the plurality of radiation images, based on the positional information acquired by the position acquiring unit, before acquiring the radiation images from the plurality of radiation imaging apparatuses.

11. A radiographing system, comprising:
a plurality of radiation imaging apparatuses each of which acquires a radiation image;
a composition processing unit which composites a plurality of radiation images acquired from the plurality of radiation imaging apparatuses to generate a long-length image, wherein
a posture acquiring unit acquires information regarding a posture of at least one radiation imaging apparatus among the plurality of radiation imaging apparatuses is provided, and
a position deciding unit decides an order, in which the plurality of radiation images to be composited by the composition processing unit are composited, based on the information regarding the posture acquired by the posture acquiring unit.

12. A radiation imaging apparatus which acquires a radiation image and is configured to be used in a radiographing system which composites a plurality of radiation images to generate a long-length image, the radiation imaging apparatus comprising:
a position acquiring unit which acquires positional information of the radiation imaging apparatus at the time of acquiring the radiation image; and
a transmission unit which transmits the positional information acquired by the position acquiring unit to a position deciding unit in the radiographing system,
wherein the radiographing system decides an order in which the plurality of radiation images are composited, based on the positional information.

13. A method of controlling a radiographing system which has a plurality of radiation imaging apparatuses, each of which acquires a radiation image, and a composition processing unit which composites a plurality of radiation images acquired from the plurality of radiation imaging apparatuses to generate a long-length image, the method comprising:
a step of acquiring positional information from each of the plurality of radiation imaging apparatuses; and
a step of deciding an order, in which the plurality of radiation images to be composited by the composition processing unit are composited, based on the positional information.

14. A recording medium storing therein a computer program for causing a computer to execute the controlling method according to claim 13.

15. A radiographing system, comprising:

a plurality of radiation imaging apparatuses each of which has a radiation detecting panel, the radiation detection panel has a plurality of pixels arrayed in a two-dimensional matrix and converts radiated radiation into an image signal for a radiation image; and a control apparatus which composites a plurality of radiation images acquired from the plurality of radiation imaging apparatuses to generate a long-length image, wherein each of the plurality of radiation imaging apparatuses includes a position acquiring unit which acquires positional information from an external apparatus; and the control apparatus decides an order, in which the plurality of radiation images are composited, based on the positional information acquired by the position acquiring unit.

16. The radiographing system according to claim 15, wherein the external apparatus is an apparatus which can hold and provide the positional information.

\* \* \* \* \*